United States Patent [19]

Turner

[11] 4,047,687
[45] Sept. 13, 1977

[54] VERTICALLY ADJUSTABLE SUPPORT

[76] Inventor: Kathleen Harding Turner, 930 Delaine, Corpus Christi, Tex. 78411

[21] Appl. No.: 693,891

[22] Filed: June 7, 1976

[51] Int. Cl.² ..................... A61G 12/00; A47B 73/00
[52] U.S. Cl. .................................. 248/318; 211/117; 248/333
[58] Field of Search ............. 248/318, 320, 322, 333, 248/339, 340, 326, 327; 211/117, 113, 118

[56] References Cited

U.S. PATENT DOCUMENTS

| 32,147 | 4/1861 | Robinson | 248/333 X |
|---|---|---|---|
| 495,409 | 4/1893 | Fry | 248/333 X |
| 1,005,870 | 10/1911 | Packer | 248/340 X |
| 1,585,547 | 5/1926 | Jones | 248/340 |
| 3,191,904 | 6/1965 | Karapita | 248/333 |

FOREIGN PATENT DOCUMENTS 836,849  4/1952  Germany ................. 248/333

Primary Examiner—J. Franklin Foss
Attorney, Agent, or Firm—G. Turner Moller

[57] ABSTRACT

There is disclosed a vertically telescoping support, the outer member of which is provided with a hook for suspension from a suitable object. A plurality of J-slots in the outer member cooperates with a like plurality of radially extending pins on the inner member for positioning the inner member at a plurality of telescoped locations relative to the outer member. The pins also provide a plurality of vertically spaced supports for an object, such as a water container for a colostomy irrigator.

9 Claims, 3 Drawing Figures

VERTICALLY ADJUSTABLE SUPPORT

In order to irrigate a colostomy in accordance with present techniques, one individual is required to hold the water reservoir while another person manipulates the irrigation tube. The elevation of the water reservoir is important in order to control the water pressure at the discharge end of the irrigation tube. If the water reservoir is too low, discharge water pressure is too low thereby contributing to ineffective cleaning. If the water reservoir is too high, discharge water pressure is too high which may be very painful to the patient, particularly if the patient is still recovering from the colostomy operation. It is accordingly essential to maintain the water reservoir at a desired level thus requiring an individual to hold it, which can be very tiring.

It would accordingly be desirable to provide a vertically adjustable support which could be suspended from any suitable object and which provides a plurality of vertically spaced locations at which a water reservoir could be supported. In addition to colostomy irrigations, it is immediately apparent that such a device would be highly desirable for rectal irrigations, enemas, feminine hygiene douches, blood transfusions, intravenous feedings and the like.

Of interest with respect to this invention are the disclosures in U.S. Pat. Nos. 479,090 and Design 228,878.

It is an object of this invention to provide a vertically adjustable support which can be readily hung on any suitable object and which provides a plurality of support locations for a water reservoir.

In summary, this invention comprises a longitudinally adjustable support assembly providing a plurality of support positions for a supported article, including first and second elongate longitudinally adjustable members, means on one of the members for suspending the same from a support, means for latching the first and second members together in a plurality of positions including at least one pin on the first member, a plurality of longitudinally spaced J-slots provided on the second member for supporting the pin and the first member, and means allowing movement of the pin between the plurality of J-slots, and means for supporting an article from the assembly comprising a plurality of support elements carried by the other member and extending transverse to the axis of the members.

Figures 1, 2, 3:
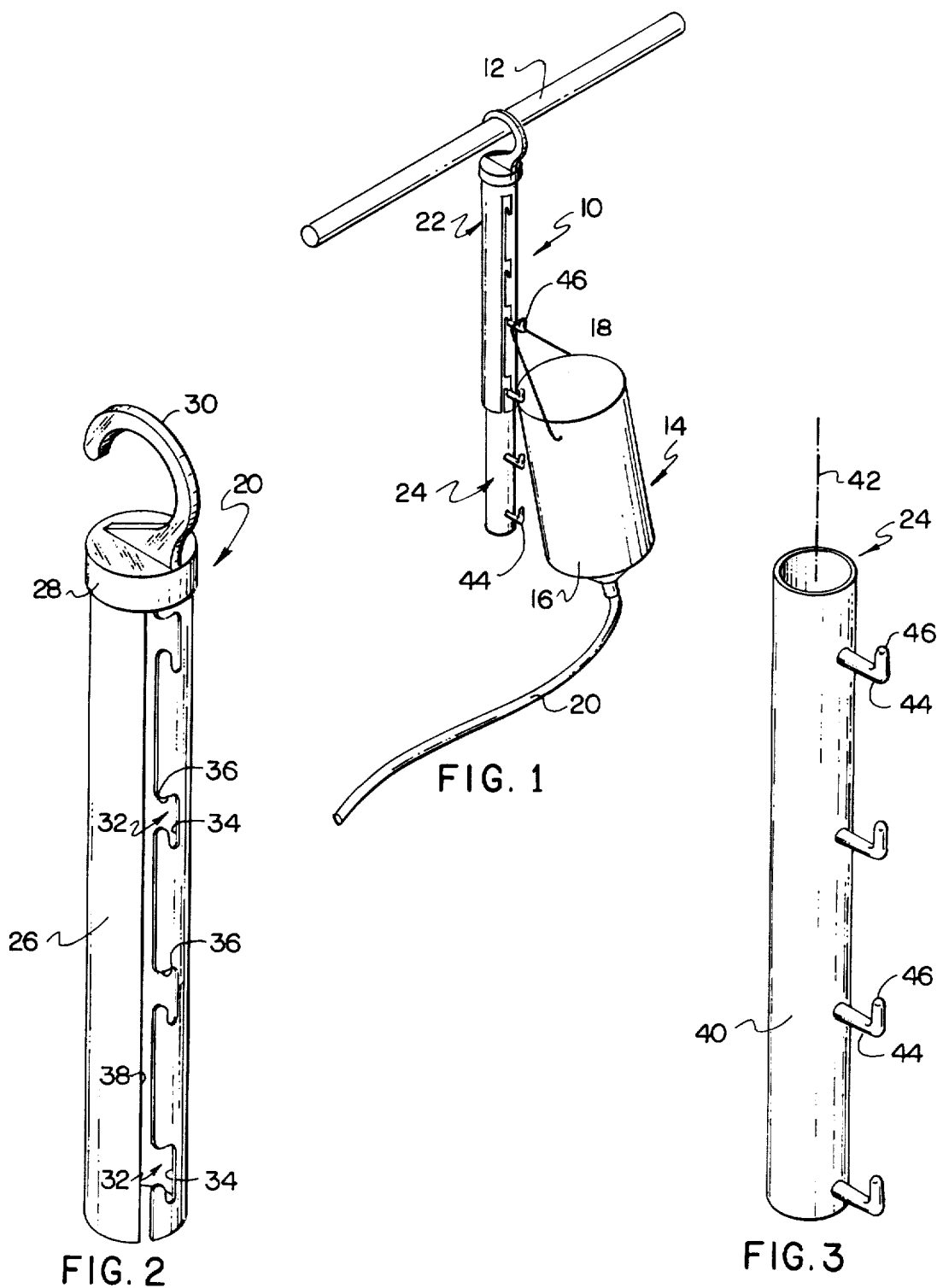
FIG. 1 is an isometric view of a vertically adjustable support assembly made in accordance with the principles of this invention and illustrated in operative position.
FIG. 2 is an enlarged isometric view of an outer telescoping member comprising part of the adjustable support assembly of this invention.
FIG. 3 is an enlarged isometric view of an inner telescoping member of this invention.

Referring to FIG. 1, there is illustrated a vertically adjustable support assembly 10 of this invention illustrated as suspended from a shower curtain rod 12 and supporting an irrigation unit 14 comprised of a water container or reservoir 16 having a bail or handle 18 and an irrigation tube 20. The support 10 comprises an outer tube or member 22 and an inner tube or member 24 telescoped together.

The outer tube 22 comprises an elongate hollow member 26 of metal, plastic or the like having an end cap 28 rigidly secured thereto. Projecting upwardly from the cap 28 is a hook 30 or other suitable support member for suspending the tube 22 from the shower rod 12, towel rack, toilet paper rack, chair back, shower nozzle or other suitable object located where the irrigation unit 14 is to be used. Extending through the wall of the hollow member 26 are a plurality of longitudinally aligned, vertically spaced J-slots 32 comprising a longitudinally extending leg 34 and a peripherally or circumferentially extending leg 36, intersecting the leg 34 above the bottom thereof. A longitudinally extending linear slot 38 extends from the lower open end of the hollow member 26 and communicates with each of the circumferentially legs 36.

The inner tube 24 comprises an elongate member 40 which may be either solid or hollow, as illustrated, and may be of any suitable material. Extending radially, relative to an axis 42 of the tube 24, from the periphery of the member 40 are a plurality of longitudinally aligned, vertically spaced hangers or pins 44 having an upturned end 46. The circumferential slot legs 36 and the pins 44 are equally spaced from the next adjacent leg 36 or pin 44 respectively.

To assemble the support 10, the inner tube 24 is introduced into the lower open end of the outer tube 24, the pins 44 are aligned with the slot 38 and the tubes 22, 24 telescoped together until the overall length is as desired. By registering the pins 44 with the circumferential slot legs 36, rotating the tube 24 so that the pins 44 advance into the slots 32 and allowing the tube 24 to move downwardly relative to the tube 22 so that the pins 44 advance to the bottom of the longitudinal slot legs 34, the tube 24 is temporarily supported by the tube 22.

It will accordingly be seen that the pins 44 and J-slots 32 cooperate to provide a latch for temporarily securing the members 22, 24 together. With the uppermost pin 44 supported in the uppermost slot 32, it will be apparent that there are provided four levels or longitudinally spaced locations for supporting the bail 18 of the irrigation unit 14. By telescoping the tubes 22, 24 so that the uppermost pin 44 registers with the lowermost slot 32, it will be apparent that an additional three support levels are provided. It will also be apparent that the support 10 may be of any desired diameter or length and provide as many pins 44 as desired.

In use, the tube 22 is suspended from any suitable support, such as the shower rod 12, and the tubes 22, 24 manipulated to place one of the support pins at what is believed to be a desired elevation. The water container 16 is then raised and the bail 18 placed on one of the support pins 44. The individual may then manipulate the irrigation tube 20 in a conventional manner. If the cleaning solution emitting from the irrigation tube 20 is of insufficient pressure, the water container 16 may be elevated for support on one of the higher pins 44. If the cleaning solution pressure is too great, the container may be moved to one of the lower support pins 44. It will accordingly be apparent that the vertically adjustable support 10 allows a single individual to conduct the irrigation procedure.

I claim:

1. A longitudinally adjustable support assembly providing a plurality of support positions for a supported article, comprising first and second elongate longitudinally adjustable members;

means on the second member for suspending the same from a support;

means for latching the first and second members together in a plurality of positions including
a plurality of longitudinally spaced pins on the first member,
a plurality of longitudinally spaced J-slots provided on the second member for supporting the pin and the first member, and
means allowing movement of the pin between the plurality of J-slot; and
means for supporting an article from the assembly comprising the plurality of pins.

2. The support of claim 1 wherein the J-slots each comprise a generally longitudinal leg and a generally transverse leg and the movement allowing means comprises a generally longitudinal slot communicating with the transverse legs of the J-slots.

3. The support of claim 2 wherein the plurality of pins and the transverse leg of the J-slots are equally longitudinally spaced.

4. The support of claim 3 wherein the longitudinal slot is generally linear.

5. The support of claim 4 wherein the one member is a tube and the slots extend from the inside of the tube to the outside thereof.

6. The support of claim 5 wherein the one member is the first member, the other member is the second member and the first and second members telescope relative to each other.

7. A longitudinally adjustable support providing a plurality of support positions for a supported article, comprising
a pair of elongate longitudinally adjustable members;
means on one of the members for supporting the same from a support;
means on the other member for supporting an article; and
means for latching the first and second members together in a plurality of positions including
at least one pin on one of the members;
a plurality of longitudinally spaced J-slots provided on the other member for supporting the pin and the one member,
means allowing movement of the pin between the plurality of J-slots;
the article supporting means comprising the pin.

8. The support of claim 7 wherein the latching means comprises a plurality of pins on the one member, a plurality of the pins comprising a plurality of article supporting means.

9. The support of claim 8 wherein the plurality of pins and the plurality of J-slots are equally longitudinally spaced.

* * * * *